US000001532H

United States Statutory Invention Registration [19]

[11] Reg. Number: H1532

Adamson et al.

[45] Published: May 7, 1996

[54] ADAPTION OF MAMMALIAN CELL LINES TO HIGH CELL DENSITIES

[75] Inventors: S. Robert Adamson, Chelmsford, Mass.; Denis Drapeau, Salem, N.H.; Yen-Tung Luan, Chelmsford, Mass.; Douglas A. Miller, Salem, N.H.

[73] Assignee: Genetics Institute, Inc., Cambridge, Mass.

[21] Appl. No.: 146,860

[22] Filed: Nov. 3, 1993

[51] Int. Cl.[6] ..... C12N 5/02

[52] U.S. Cl. ..... 435/240.2; 435/240.23; 435/240.25

[58] Field of Search ..... 435/240.2, 240.23, 435/240.25

[56] References Cited

U.S. PATENT DOCUMENTS

| | | | |
|---|---|---|---|
| 4,757,005 | 7/1988 | Chan | 435/68 |
| 4,767,704 | 8/1988 | Cleveland et al. | 435/68 |
| 5,096,816 | 3/1992 | Maiorella | 435/70.21 |
| 5,122,469 | 6/1992 | Mather et al. | 435/240.2 |
| 5,147,790 | 9/1992 | Wilson | 435/70.3 |
| 5,156,964 | 10/1992 | Inlow et al. | 435/172.1 |

FOREIGN PATENT DOCUMENTS

| | | |
|---|---|---|
| 481791A2 | 4/1992 | European Pat. Off. . |
| 2195655 | 10/1989 | United Kingdom . |
| WO91/11508 | 8/1991 | WIPO . |
| WO92/13067 | 8/1992 | WIPO . |
| WO93/05145 | 3/1993 | WIPO . |

OTHER PUBLICATIONS

Avgerinos et al, BioTechnology, vol. 8, Jan. 1990, pp. 54–58.

Miller et al, American Chemical Society Abstracts of Papers, Part 1. Mar. 28–Apr. 2, 1993 (abstract 104).

Dawson, *Cell Culture,* edited by Butler et al, Chapter 2, pp. 25–27 and 222 (1992).

Griffiths, *Animal Cell Culture,* edited by Freshney, Chapter 3, pp. 33–45 (1986).

Hamilton et al., *In Vitro* v. 13, No. 9 pp. 537–547 (1977).

Ling et al., *Experimental Cell Research* v. 52 pp. 469–489 (1968).

Miller et al., *Bioprocess Engineering* v. 3 pp. 113–122 (1988).

Schumpp et al., *Cytotechnology* v. 8 pp. 39–44 (1992).

*Primary Examiner*—Donald P. Walsh
*Assistant Examiner*—Chrisman D. Carroll
*Attorney, Agent, or Firm*—Steven R. Lazar; Thomas J. DesRosier

[57] ABSTRACT

Methods and nutrient media are disclosed useful for adapting mammalian cell lines to culture at increased cell densities.

9 Claims, No Drawings

ADAPTION OF MAMMALIAN CELL LINES TO HIGH CELL DENSITIES

FIELD OF THE INVENTION

The present invention relates to improved methods of expressing proteins through culture of mammalian cell lines. In particular, the present invention relates to methods of improving the productivity of mammalian cell lines through adaption to otherwise growth-limiting conditions.

BACKGROUND OF THE INVENTION

It is known that various factors may be responsible for limiting the growth of cells at high cell densities. These factors include absence of sufficient amounts of nutrients needed by the cells for sustained growth, as well as the presence of growth-limiting concentrations of inhibitors that may be secreted by the cells in culture. One inhibitor that is secreted by mammalian cells is ammonia. See Miller et at., *Bioprocess Engineering,* 3:113–122 (1988); Inlow et at., U.S. Pat. No. 5,156,964 describes a method for generating tolerance to ammonia that involves culturing cells in a medium to which ammonia has been added. Similarly, Schumpp et at., *Cytotechnology,* 8:39–44 (1992) describe a method for generating cell lines tolerant of both ammonia and lactic acid by culturing cells in a medium to which both ammonia and lactic acid had been added.

The previous methods have several drawbacks. First, in order to generate tolerance to an inhibitor according to the above methods, it is first necessary to determine that a particular inhibitor is a growth-limiting factor for cells and then to develop a protocol for generating tolerance to that inhibitor. Second, the growth of cell lines which are generated with tolerance to a particular inhibitor according to the above methods may then be limited by a second, different inhibitor. Repeated experiments may be necessary to generate tolerance to multiple growth-limiting inhibitors in order to achieve significant increases in cell densities.

SUMMARY OF THE INVENTION

According to the present invention, many of the drawbacks of the above prior art are overcome. The present invention provides methods by which the growth-limiting factors present for a particular cell line can be overcome without first conducting time-consuming testing to identify the specific growth-limiting inhibitors.

It is one object of the present invention to provide methods of improving the productivity of mammalian cell lines.

It is another object of the present invention to provide methods for adapting cell lines to high cell densities.

It is yet another object of the present invention to provide nutrient-rich growth media in which nutrients are present in sufficient quantity so that they are not expected to limit cell growth.

According to the present invention, the above objects are largely achieved by providing methods for adapting mammalian cell lines to culture at increased cell densities. The methods of the present invention comprise adapting mammalian cell lines to grow at increased cell densities, by (a) initiating a passage by diluting a culture containing mammalian cells with a suitable growth medium by a dilution factor suitable for the passage duration; (b) maintaining pH, dissolved oxygen, and nutrients at non-limiting levels during the passage; and repeating steps (a) and (b) at least about 5 times. In a preferred embodiment of the invention, the steps are repeated about 5 to about 20 times.

The present invention further comprises methods for adapting CHO cell lines to grow to increased cell densities, comprising:

a) initiating a passage of duration aproximately 1 to 5 days by diluting a culture containing CHO cells at a density of at least approximately $1\times10^6$ cells/ml with a suitable growth medium, the dilution factor being suitable to the passage duration; (b) maintaining pH, dissolved oxygen, and nutrients in non-limiting levels during the passage; and c) repeating steps (a) and (b) at least about 5 times.

The present invention further comprises methods for adapting CHO cell lines to grow to increased cell densities comprising: (a) initiating a passage of duration approximately 3 to 4 days by diluting a culture containing CHO cells at a density of at least approximately $1\times10^6$ cells/ml with a suitable growth medium, the dilution factor being suitable to the passage duration; (b) maintaining pH, dissolved oxygen, and nutrients at non-limiting levels during the passage; and (c) repeating steps (a) and (b) at least about 5 times.

In a preferred embodiment, the present invention comprises a method for adapting mammalian cell lines to culture at increased cell densities, said method comprising continuously or periodically diluting a cell culture, containing mammalian cells, with a suitable growth medium, for between approximately 10 and 60 days, while maintaining pH, dissolved oxygen and nutrients at non-limiting levels.

Other preferred methods of the present invention comprise adapting CHO cell lines to culture at increased cell densities, said method comprising continuously or periodically diluting a culture containing CHO cells, at a density of at least approximately $1\times10^6$ cells/ml with a suitable growth medium, the dilution rate being less than approximately 0.029 $hr^{-1}$, while maintaining pH, dissolved oxygen and nutrients at non-limiting levels. Preferred dilution rates are between approximately $0.018hr^{-1}$ and $0.026hr^{-1}$.

DETAILED DESCRIPTION OF THE INVENTION

Mammalian cell lines are used for the production of commercially useful proteins. Some mammalian cell lines which are commonly used include chinese hamster ovary (CHO) cell lines, hybridomas, monkey COS-1 cells, HeLa cells, melanoma cell lines such as the Bowes cell line, hybridoma cell lines, mouse L cells, mouse fibroblasts, mouse NIH 3T3 cells and the CV-1 cell line. In the present invention, these and other mammalian cell lines may be adapted for culture at high cell densities.

Suitable growth media for the present invention include any medium which provides nutrients at non-limiting levels. Nutrients will generally be at non-limiting levels if raising concentrations of all nutrients results in no increase in growth rate. Nutrient concentrations may be maintained at non-limiting levels by either providing excess amounts of all nutrients in the fresh medium or by adding nutrients to the culture as they are taken up by the cells or degraded. A suitable growth medium for mammalian cell lines is disclosed in Ling et al., *Experimental Cell Research;* 52:469–489 (1968). Accordingly, one preferred growth medium contains the amino acid nutrients in the concentrations disclosed in Table 1.

TABLE 1

| Column I NUTRIENT | Column II CONCEN-TRATION RANGE (MG/L) | Column III OPTIMAL CONCENTRATION (MG/L) |
|---|---|---|
| L-asparagine $H_2O$ | 30–360 | 540 |
| L-aspartic acid | 69–798 | 266 |
| Glycine | 30–450 | 60 |
| L-isoleucine | 79–948 | 472 |
| L-leucine | 158–1890 | 681 |
| L-lysine HCl | 229–2742 | 728 |
| L-methionine | 75–894 | 238 |
| L-serine | 79–948 | 630 |
| L-threoine | 90–1074 | 381 |
| L-tryptophan | 31–366 | 131 |
| L-tyrosine 2Na $2H_2O$ | 65–783 | 418 |

TABLE 1-continued

| Column I NUTRIENT | Column II CONCEN-TRATION RANGE (MG/L) | Column III OPTIMAL CONCENTRATION (MG/L) |
|---|---|---|
| L-valine | 141–1686 | 374 |

Other nutrients which may be addded to the medium include inorganic salts, such as chlorides, phosphates, sulfates and nitrates, sugars, vitamins, and additives such as glutamine, pyruvate, linoleic, thioctic, selenite, hydrocortisone, insulin.

Other preferred growth media suitable for mammalian cell lines include a medium containing the components described in Table 2 below.

TABLE 2

| | NUTRIENT COMPOSITION OF MEDIUM | | |
|---|---|---|---|
| Column I Components | Column II Medium proposed by Ling et al. (mg/L) (1968) | Column II Medium used for adaptation in Example (mg/L) | Column IV Preferred non-limiting medium (mg/L) |
| sodium chloride | 7000 | 4600 | 4400 |
| potassium chloride | 375 | 624 | 310 |
| calcium chloride, anhydrous | 156 | 232 | 58 |
| sodium phosphate, dibasic, anhydrous | | 142 | |
| sodium phosphate, monobasic, hydrate | | 125 | 130 |
| magnesium chloride, anhydrous | | 57 | |
| magnesium sulfate, anhydrous | 120 | 98 | 84 |
| cupric sulfate, anhydrous | 185 | 0.0016 | 0.0018 |
| ferrous sulfate, anhydrous | | 0.68 | 0.91 |
| ferric nitrate, nonahydrate | 1.2 | 0.10 | |
| zinc sulfate, septahydrate | 0.86 | 0.86 | 0.92 |
| sodium selenite | | 0.010 | 0.010 |
| sodium bicarbonate | | 2440 | 2400 |
| L-alanine | 45–534 | 36 | 71 |
| L-arginine | 218–2616 | 600 | 760 |
| L-asparagine hydrate | 30–360 | 180 | 540 |
| L-aspartic acid | 67–798 | 133 | 270 |
| L-cysteine hydrochloride hydrate | | 282 | 700 |
| L-cystine dihydrochloride | 23–281 | 125 | |
| L-glutamic acid | 103–1236 | 59 | 120 |
| L-glutamine | 212–2544 | 1168 | 1200 |
| glycine | 38–450 | 60 | 60 |
| L-histidine hydrochloride hydrate | 105–1260 | 126 | 290 |
| L-isoleucine | 79–948 | 210 | 470 |
| L-leucine | 158–1890 | 260 | 680 |
| L-lysine hydrochloride | 229–2742 | 291 | 730 |
| L-methionine | 75–894 | 104 | 240 |
| L-phyenylalanine | 99–1188 | 165 | 330 |
| L-proline | 86–1032 | 138 | 280 |
| L-serine | 79–948 | 315 | 630 |
| L-threoinie | 90–1074 | 190 | 380 |
| L-tryptophan | 31–366 | 33 | 130 |
| L-tryosine disodium dihydrate | 57–678 | 262 | 420 |
| L-valine | 141–1686 | 187 | 370 |
| biotin | 0.03 | 0.41 | 1.6 |
| D-calcium pantothenate | 5.0 | 4.5 | 18 |
| choline chloride | 350 | 18 | 72 |
| folic acid | 0.10 | 5.3 | 21 |
| i-inositol | 35 | 25 | 100 |
| nicotinamide | 20 | 4.0 | 16 |
| pyridoxine hydrochloride | | 0.062 | 16 |
| pyridoxal hydrochloride | 2.5 | 4.0 | |
| riboflavin | 1.5 | 0.44 | 1.8 |
| thiamine hydrochloride | 1.0 | 4.3 | 18 |
| vitamin B12 | 0.003 | 1.6 | 5.6 |
| D-glucose | 2000 | 6000 | 6200 |
| sodium pyruvate | | 110 | |

TABLE 2-continued

| NUTRIENT COMPOSITION OF MEDIUM | | | |
|---|---|---|---|
| Column I Components | Column II Medium proposed by Ling et al. (mg/L) (1968) | Column II Medium used for adaptation in Example (mg/L) | Column IV Preferred non-limiting medium (mg/L) |
| linoleic acid | 0.21 | 0.084 | 0.17 |
| thioctic acid | 0.70 | 0.21 | 0.42 |
| putrescine dihydrochloride | | 2.2 | 2.0 |
| polyvinyl alcohol | | 2400 | 2400 |
| insulin or Nucellin | 1.0 | 10 | 10 |
| hydrocortisone | | 0.072 | 0.072 |
| methotrexate | | 1.3 | |
| soybean phospholipid | | 10 | |
| fetal bovine serum | | 5000 | |
| B-glycerophosphate, disodium | 1000 | | |
| D-sorbitol | 100 | | |
| oxalacetic acid | 65 | | |
| thymidine | 10 | | |
| deoxycytidine | 11 | | |
| homocysteine thiolactate | 8–90 | | |
| glutathione, reduced | 31–372 | | |
| sodium molybdate, dihydrate | 0.015 | | |
| vitamin A acetate | 1.0 | | |
| vitamin D3 | 0.005 | | |
| a-tocopherol | 7.0 | | |
| oleic acid | 0.2 | | |
| arachidonate, methyl | 0.02 | | |
| cholesterol | 5 | | |
| ovo-lecithin | 25 | | |
| ethanol | 2000 | | |

Suitable dilution factors (for passaging) and suitable dilution rates (for continuous culture) appropriate for adapting a particular mammalian cell line to grow to increased cell densities may be calculated using the formulas:

$$\text{dilution factor}=e^{(\mu t)}$$

$$\text{dilution rate}=\mu$$

where t is the duration in hours of the upcoming passage and $\mu$ is any quantity less than $\mu_{max}$, preferably a quantity between approximately ($0.6\times\mu_{max}$) and approximately ($0.9\times\mu_{max}$). $\mu_{max}$ in hour$^{-1}$, is the specific growth rate of the cell line when none of the following extracellular factors limits growth: pH, dissolved oxygen, nutrient depletion and cell-generated inhibitors.

The magnitude of $\mu_{max}$ may be estimated without precise measurement in a variety of ways. For example, an estimate of $\mu_{max}$ may be generated as follows. First the maximum cell density attainable in a spinner flask using a common medium (such as a 1:1 mixture of DME and F12) is determined by suspending growth phase cells in this medium in the spinner flask and measuring the cell density on each subsequent day until cell density no longer rises. Next, growth phase cells are suspended in fresh medium in another spinner flask at a starting density approximately 10-fold below the maximum attainable density and cultured for approximately 2 days. This culture is diluted with fresh medium to the same starting cell density every two days for several passages. The estimate of $\mu_{max}$ is the growth rate observed during these passages, calculated using the following formula:

$$\mu max=(\ln X_f-\ln X_i)/t$$

where $X_r$ is the cell density at the end of a typical passage, $X_i$ is the cell density at the beginning of the same passage, and t is the duration of the passage in hours.

For CHO cell lines, a suitable dilution factor for a given duration of passage may be as follows: If the passage is approximately 1 day, a suitable dilution factor is less than about 2, preferably from about 1.5 to about 2. If the passage duration is approximately 2 days, a suitable dilution factor is less than about 4, preferably from about 2 to about 4. If the passage duration is approximately 3 days, a suitable dilution factor is less than about 8, preferably from about 3 to about 7. If the passage duration is approximately 4 days, suitable dilution factors are less than about 16, preferably from about 5 to about 13. If the passage duration is approximately 5 days, a suitable dilution factor is less than about 32, preferably from about 9 to about 23. For other mammalian cell lines, suitable dilution factors may be calculated on the basis of the maximum growth rate of the cell line. The maximum growth rate for a cell line may be determined as described above.

In the method of the present invention, relatively constant levels of pH, dissolved oxygen, and nutrients are maintained at non-limiting levels during the passage. This may preferably be accomplished by performing the adaption process in a bioreactor. pH may be maintained at the proper pH by addition of a suitable alkaline or acidic additive or buffer, for example sodium carbonate and sodium bicarbonate. Dissolved oxygen may be maintained by introduction of oxygen or air bubbles. If necessary, nutrient levels may be maintained by the addition of those nutrients which are depleted, or by addition of fresh growth medium.

In the present invention, mammalian cell lines, such as CHO cell lines, may be cultured at a suitable cell density, which may be approximately $1\times10^6$ cells/ml, in a suitable growth medium, and may be diluted in accordance with the above description.

The present invention is illustrated by the following examples. These examples do not limit the invention in any manner. It is contemplated that minor improvements and variations may be made which are part of the present invention.

EXAMPLES

The recombinant chinese hamster ovary cell (CHO) line E5F3G expresses recombinant human M-CSF, as described in Clark et at., U.S. Pat. Nos. 4,868,119 and 4,879,227. As described below, the E5F3G cell line was adapted to grow to increased cell densities, and thereby generate higher concentrations of rhM-CSF.

E5F3G cells from a spinner flask were grown to a density of $1.24\times10^6$ cells/ml in approximately 1000 ml of a nutrient-rich medium (Table 2) in a 2-L bioreactor (passage 1 in Table 3).

These cells were then cultured for an additional ten 3-day or 4-day passages in the 2-L bioreactor (passages 2 through 11) in the nutrient-rich medium. During each passage, pH was maintained at between 7.0 and 7.2 by addition of sodium carbonate and sodium bicarbonate and dissolved oxygen was maintained at between 20% and 60% of air saturation by introduction of oxygen bubbles. Each 3-day passage was started by diluting the culture from the preceding passage by a factor between 5.1 and 6.3, while each 4-day passage was started by diluting the culture from the preceding passage by a factor between 6.0 and 14.3.

The beneficial effect on the cell line was evident during two subsequent passages (passages 12 and 13). For example, in passage 12, which was started at a density of $0.50\times10^6$ cells/ml, cell density reached $4.90\times10^6$ cells/ml, and rhM-CSF titer reached 32.6 ug/ml. In contrast, in passage 4, which had been started at a higher cell density ($0.59\times10^6$ cells/ml), cell density had reached only $2.44\times10^6$ cells/ml and rhM-CSF titer had reached only 14.9 ug/ml.

TABLE 3

Adaptation of E5F3G cell line to increased cell densities

| Passage number | Passage length (days) | Dilution ratio | Initial density ($10^6$/ml) | Final density ($10^6$/ml) | Final titer (ug/ml) |
|---|---|---|---|---|---|
| 1 | 4 | — | 0.12 | 1.24 | 11.6 |
| 2 | 3 | 5.4 | 0.23 | 1.96 | 14.3 |
| 3 | 3 | 6.3 | 0.31 | 3.00 | 16.5 |
| 4 | 3 | 5.1 | 0.59 | 2.44 | 14.9 |
| 5 | 4 | 12.2 | 0.20 | 1.79 | — |
| 6 | 4 | 6.0 | 0.30 | 3.50 | — |
| 7 | 3 | 5.0 | 0.70 | 2.25 | 12.2 |
| 8 | 3 | 5.2 | 0.43 | 2.70 | 15.6 |
| 9 | 4 | 12.3 | 0.22 | 4.30 | 20.2 |
| 10 | 4 | 14.3 | 0.30 | 5.90 | 29.2 |
| 11 | 3 | 5.9 | 1.00 | 5.70 | 33.5 |
| 12 | 3 | 11.4 | 0.50 | 4.90 | 32.6 |
| 13 | 4 | 16.3 | 0.30 | 5.30 | 34.2 |

We claim:

1. A method for producing an adapted mammalian cell line which grows at increased cell densities, said method comprising:

a) initiating a passage by diluting a culture containing mammalian cells with a suitable growth medium, the dilution factor being suitable for the duration of the passage;

b) maintaining pH, dissolved oxygen, and nutrients at non-limiting levels during the passage;

c) repeating steps (a) and (b) at least about 5 times; and d) obtaining an adapted mammalian cell line with the ability to grow at increased cell densities.

2. The method of claim 1, wherein steps (a) and (b) are repeated about 5 to about 20 times.

3. A method for producing an adapted CHO cell line which grows at increased cell densities, said method comprising:

a) initiating a passage approximately 1 to 5 days in duration by diluting a culture containing CHO cells at a density of at least approximately $1\times10^6$ cells/ml with a suitable growth medium, the dilution factor being suitable for the duration of the passage;

b) maintaining pH, dissolved oxygen, and nutrients in non-limiting levels during the passage;

c) repeating steps (a) and (b) at least about 5 times; and d) obtaining an adapted CHO cell line with the ability to grow at increased cell densities.

4. The method of claim 3, wherein steps (a) and (b) are repeated about 5 to about 20 times.

5. A method for producing an adapted CHO cell line which grows at increased cell densities, said method comprising:

a) initiating a passage approximately 3 to 4 days in duration by diluting a culture containing CHO cells at a density of at least approximately $1\times10^6$ cells/ml with a suitable growth medium, the dilution factor being suitable to the duration of the passage;

b) maintaining pH, dissolved oxygen, and nutrients at non-limiting levels during the passage;

c) repeating steps (a) and (b) at least about 5 times; and d) obtaining an adapted CHO cell line with the ability to grow at increased cell densities.

6. The method of claim 5, wherein steps (a) and (b) are repeated about 5 to about 20 times.

7. A method for adapting mammalian cell lines to culture at increased cell densities, said method comprising continuously or periodically diluting a cell culture, containing mammalian cells, with a suitable growth medium, for between approximately 10 to 60 days, while maintaining pH, dissolved oxygen and nutrients at non-limiting levels.

8. A method for adapting CHO cell lines to culture at increased cell densities, said method comprising continuously or periodically diluting a culture containing CHO cells, at a density of at least approximately $1\times10^6$ cells/ml with a suitable growth medium, at a dilution rate less than approximately 0.029 $hr^{-1}$, while maintaining pH, dissolved oxygen and nutrients at non-limiting levels.

9. The method of claim 8, wherein the dilution rate is between approximately 0.018 $hr^{-1}$ and 0.026 $hr^{-1}$.

* * * * *